United States Patent [19]

Sato et al.

[11] Patent Number: 5,523,396
[45] Date of Patent: Jun. 4, 1996

[54] PROCESS FOR SYNTHESIZING QUINONEDIAZIDE ESTER UTILIZING BASE CATALYST

[75] Inventors: Kenichiro Sato; Yasumasa Kawabe; Toshiaki Aoai, all of Shizuoka, Japan

[73] Assignee: Fuji Photo Film Co., Ltd., Kanagawa, Japan

[21] Appl. No.: 531,861

[22] Filed: Sep. 21, 1995

[30] Foreign Application Priority Data

Oct. 5, 1994 [JP] Japan .................................. 6-241354
Oct. 31, 1994 [JP] Japan .................................. 6-267490

[51] Int. Cl.$^6$ ........................... G03F 7/022; G03F 7/023
[52] U.S. Cl. ......................... 534/557; 430/190; 430/193
[58] Field of Search .................................. 430/168, 169, 430/190, 191, 192, 193; 534/556, 557

[56] References Cited

U.S. PATENT DOCUMENTS 5,250,669  10/1993  Ogawa et al. ........................ 534/557
5,272,036  12/1993  Tani et al. ........................... 430/191

*Primary Examiner*—Charles L. Bowers, Jr.
*Assistant Examiner*—Christopher G. Young
*Attorney, Agent, or Firm*—Sughrue, Mion, Zinn, Macpeak & Seas

[57] ABSTRACT

A process for synthesizing a quinonediazide ester is disclosed in which the esterification reaction of a polyhydroxy compound with 1,2-naphthoquinonediazide-5-(and/or -4-)sulfonyl chloride is carried out in the presence of a base catalyst comprising a basic compound represented by formula (I) or (II):

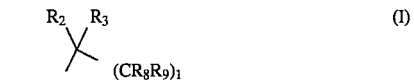

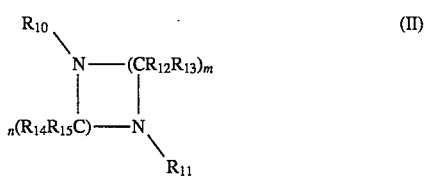

wherein $R_1$ to $R_{15}$ are defined in the disclosure. A positive working photoresist containing the ester is also disclosed. The process is capable of highly selectively yielding the desired photosensitive material containing specific unreacted hydroxyl group(s). The photoresist has high resolving power with reduced film thickness dependence of the resolving power, is less apt to leave a development residue, and has excellent storage stability for prolonged period of time.

2 Claims, No Drawings

PROCESS FOR SYNTHESIZING QUINONEDIAZIDE ESTER UTILIZING BASE CATALYST

FIELD OF THE INVENTION

The present invention relates to a process for synthesizing a quinonediazide ester for use in processes for producing semiconductors, e.g., IC's, or circuit boards for liquid-crystal devices, thermal heads, etc., and in other photofabrication processes. This invention also relates to a positive working photoresist containing the quinonediazide ester obtained by the synthesis process, more particularly a positive working photoresist for fine processing use which attains high resolving power regardless of fluctuation in the film thickness, generates a less development residue and has a satisfactory stability for a prolonged period of time.

BACKGROUND OF THE INVENTION

Positive working photoresist compositions in general use comprise an alkali-soluble resin binder, e.g., a novolak, and a naphthoquinonediazide compound as a photosensitive material.

Such a positive working photoresist is applied on a substrate such as a semiconductor wafer, glass, a ceramic, or a metal by spin coating or roller coating at a thickness of from 0.5 to 2 μm. The coating is dried by heating, and then irradiated with, e.g., ultraviolet ray through an exposure mask to cure the coating in the form of, e.g., a circuit pattern. If desired, the exposed coating is baked. Thereafter, the coating is developed to form a positive image. By etching the substrate using this positive image as a mask, the surface of the substrate can be pattern-wise processed.

The novolak resin thus used as a binder not only is soluble in an aqueous alkali solution without being swelled by the solution, but also forms an image-bearing film which can be used as an etching mask having high resistance particularly to plasma etching. Consequently, novolak resins are especially useful in this application. On the other hand, the naphthoquinonediazide compound, which is used as a photosensitive material, is unique in that it itself functions as a dissolution inhibitor to reduce the alkali solubility of the novolak resin while it decomposes upon irradiation with light to yield an alkali-soluble substance thereby serving to enhance, rather than reduce, the alkali solubility of the novolak resin. Thus, due to this large change in its property upon light irradiation, naphthoquinonediazide compounds are useful especially as a photosensitive material in positive working photoresists.

From the standpoints described above, a large number of positive working photoresists comprising a novolak resin and a photosensitive naphthoquinonediazide compound have so far been developed and put to practical use. In particular, the recent progress of resist materials in improvements for higher resolving power is remarkable, and such improved resist materials have succeeded in giving sufficient results in processing for forming patterns having line widths as small as the order of submicrons.

It has conventionally been thought that use of a resist having a high contrast (γ value) is advantageous for heightening the resolving power and reproducing images with a satisfactory pattern shape, and techniques for obtaining resist compositions suited for such purposes have been developed. These techniques are disclosed in a very large number of publications. In particular, with respect to the novolak resins used as a major component of positive working photoresists, many patent applications have been made concerning monomer composition, molecular weight distribution, synthesis method, etc., and such techniques have succeeded in attaining a certain degree of satisfactory results. Also with respect to the photosensitive material as the other major component, a large number of compounds of different structures regarded as effective in attaining higher contrast have been disclosed. As a result, it has become possible to utilize these techniques to develop an ultrahigh-resolution positive working photoresist capable of resolving a pattern having a size almost equal to the wavelength of a light.

However, the degree of integration in integrated circuits is becoming higher increasingly, and the production of substrates for semiconductor circuits, e.g., VLSI's (very large scale integrated circuit), has come to necessitate a processing for forming an ultrafine pattern having a line width of 0.5 μm or smaller. The photoresists for use in this application are required to attain high resolving power especially stably and have a wide development latitude so as to ensure a constant pattern line width always. The photoresists are also required not to leave a residue on the developed resist pattern so as to prevent the circuit from having processing defects.

On the other hand, it has been found that in the formation of an ultrafine pattern, in particular, one having a line width of 0.5 μm or smaller, there is a phenomenon in which even though a certain degree of resolving power is obtained at a certain coating film thickness, this resolving power deteriorates upon a slight change in coating film thickness (hereinafter, this phenomenon is referred to as "film thickness dependence"). It has surprisingly been also found that when the film thickness changes by only a few hundredths of a micrometer, the resolving power changes considerably, and that all the representative positive working photoresists currently on the market more or less show this tendency. Specifically, when the thickness of an unexposed resist film varies from the intended film thickness in the range of $\lambda/4$ n ($\lambda$ is exposure wavelength and n is the refractive index of the resist film at that wavelength), the resulting resolving power fluctuates accordingly.

The presence of this problem of film thickness dependence was pointed out in, e.g., *SPIE Proceedings*, Vol. 1925, p. 626 (1993), where there is a description to the effect that the film thickness dependence is caused by multiple light reflection in the resist film.

This film thickness dependence has been found to be enhanced in most cases particularly when resist contrast is heightened so as to obtain a high resolving power and a pattern having a rectangular section. In the actual processing of a semiconductor substrate, a pattern is formed from a resist film whose thickness slightly varies from part to part due to the surface roughness of the substrate and unevenness of coating thickness. Therefore, this film thickness dependence has been an obstacle to the pattern formation in which a positive working photoresist is used to conduct fine processing at a resolution close to its resolution limit.

To heighten resolving power, many photosensitive material obtained by the reaction of a polyhydroxy compound having a specific structure with a 1,2-naphthoquinonediazide compound have been proposed so far. These compounds are disclosed in, e.g., JP-A-57-63526, JP-A-60-163043, JP-A-62 -10645, JP-A-62-10646, JP-A-62-150245, JP-A-63-220139, JP-A-64-76047, JP-A-1-189644, JP-A-2-285351, JP-A-2-296248, JP-A-2-296249, JP-A-3-48249, JP-A-3-48250, JP-A-3-158856, JP-A-3 -228057, JP-A-4-502519

(Tokkohyo), U.S. Pat. Nos. 4,957,846, 4,992,356, 5,151,340, and 5,178,986, and European Patent 530 148. (The terms "JP-A" as used herein means an "unexamined published Japanese patent application".) However, these photosensitive material are insufficient from the standpoint of reducing the film thickness dependence.

On the other hand, it has been known that a resist having high contrast and high resolving power is obtained by utilizing a photosensitive material having a hydroxyl group in the molecule. This technique is described in, e.g., JP-B-37-18015, JP-A-58-150948, JP-A-2-19846, JP-A-2-103543, JP-A-3-228057, JP-A-5-323597, JP-A-6-148878, JP-A-6-167805, JP-A-6-202321, U.S. Pat. Nos. 3,061,430, 3,130,047, 3,130,048, 3,130,049, 3,102,809, 3,184,310, 3,188,210, and 3,180,733, West German Patent 938233, *SPIE Proceedings*, Vol. 631, p.210, *SPIE Proceedings*, Vol. 1672, p. 231 (1992), *SPIE Proceedings*, Vol. 1672, p. 262 (1992), and *SPIE Proceedings*, Vol. 1925, p. 227 (1993). (The term "JP-B" as used herein means an "examined Japanese patent publication".)

In JP-A-3-228057, the present inventors proposed the following three methods for preparing such a photosensitive material having a hydroxyl group in the molecule.

1. An ordinary polyhydroxy compound is reacted with 1,2-naphthoquinonediazide-5-(and/or -4-)sulfonyl chloride by esterification reaction to obtain a mixture of various esters, and the desired ester (photosensitive material having a hydroxyl group in the molecule) is isolated from the mixture by column chromatography.

2. Selective reactivity with 1,2-naphthoquinonediazidesulfonyl chloride is imparted to hydroxyl groups of a polyhydroxy compound by means of an electronic or steric effect to thereby enable the polyhydroxy compound to undergo a selective esterification reaction.

3. A predetermined proportion of the hydroxyl groups of a polyhydroxy compound are protected, and the remaining hydroxyl groups are reacted with 1,2-naphthoquinonediazidesulfonyl chloride. After the esterification, the protecting groups are removed to recover hydroxyl groups.

Although Method 1 is possible on an experimental scale, Methods 2 and 3 are suitable for industrial production. However, Method 3 has a problem concerning the stability of the 1,2-naphthoquinonediazide group under the conditions used for eliminating the protecting groups. Hence, Method 2 is the most desirable.

Examples of the selectively esterifiable polyhydroxy compound used in Method 2, which has been obtained by imparting selective reactivity with 1,2-naphthoquinonediazidesulfonyl chloride to its hydroxyl groups by means of an electronic or stearic effect, include the following compounds [III] to [V], which are described in JP-A-2-19846, JP-A-2-103543, *SPIE Proceedings*, Vol. 1672, p. 231 (1992), and *SPIE Proceedings*, Vol. 1925, p. 227 (1993).

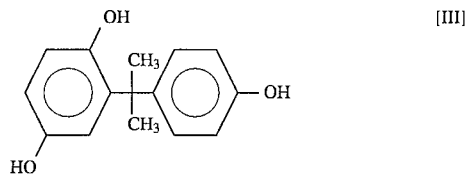

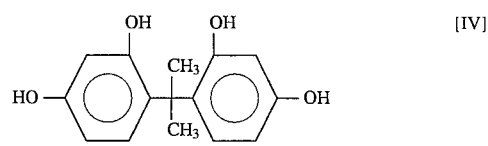

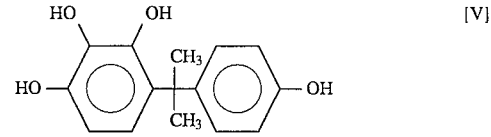

Use of compound [III] or [IV] gives a diester in high yield, while use of compound [V] gives a triester in high yield.

Examples of polyhydroxy compounds which produce a similar effect are described in JP-A-3-228057 and *SPIE Proceeding*, Vol. 1672, p. 262 (1992), i.e., compounds [VI] and [VII] shown below and the compounds represented by the following formulae [VIII] and [IX].

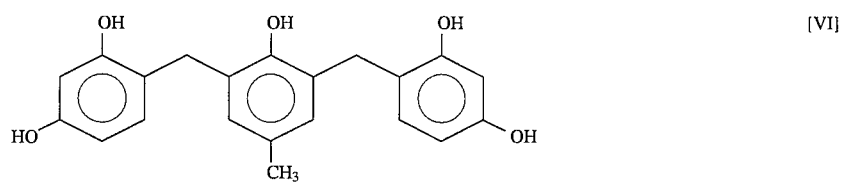

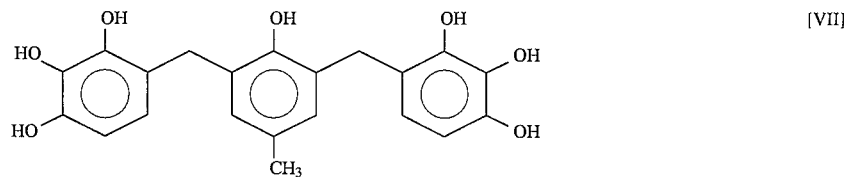

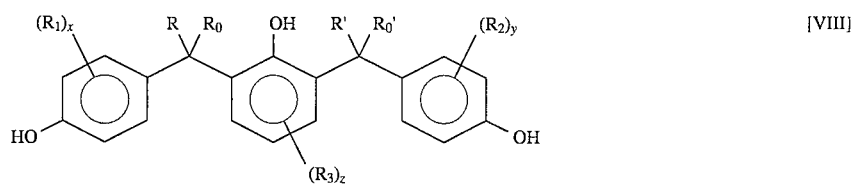

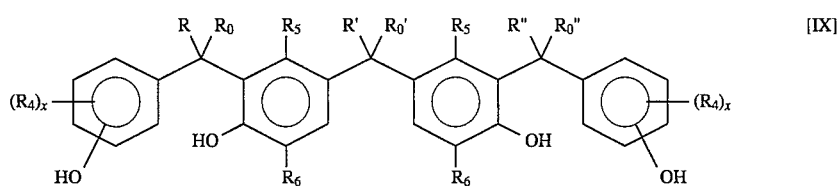

In formulae [VIII] and [IX], $R_1$, $R_2$, and $R_4$ each represents a hydrogen atom, a halogen atom, an alkyl group, a cycloalkyl group, an aryl group, or an alkoxy group (provided that the benzene rings to which $R_1$, $R_2$, or $R_4$ is bonded each has at least one hydrogen atom at the ortho position with respect to the hydroxyl group);

$R_3$ and $R_5$ each represents a hydrogen atom, an alkyl group, a cycloalkyl group, an aryl group, or an alkoxy group;

$R_6$ represents an alkyl group, a cycloalkyl group, an aryl group, or an alkoxy group;

R, R', R", $R_0$, $R_0'$, and $R_0''$ each represents a hydrogen atom or an alkyl group (provided that R and $R_0$, R' and $R_0'$, and R" and $R_0''$ may be bonded to each other to form a ring); and x, y, and z is from 1 to 3.

Use of compound [VI] gives a tetraester in high yield, use of compound [VII] gives a hexaester in high yield, and use of compound [VIII] or [IX] gives a diester in high yield.

Further examples thereof include the following compounds [X] to [XII] and compounds [XIII] to [XVI], which are described in JP-A-5-323597 and JP-A-6-167805.

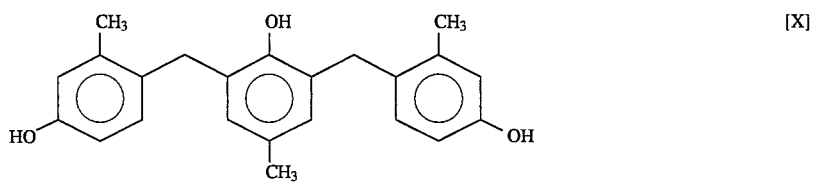

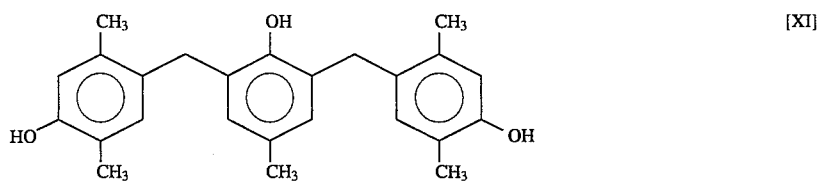

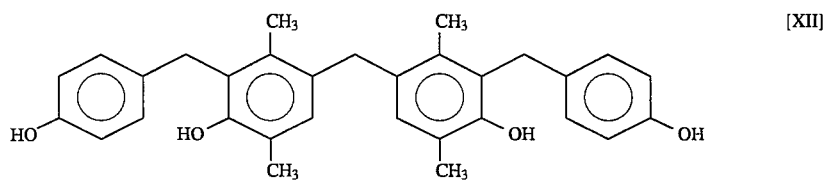

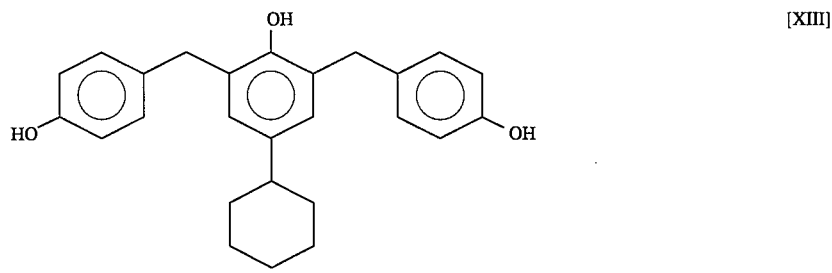

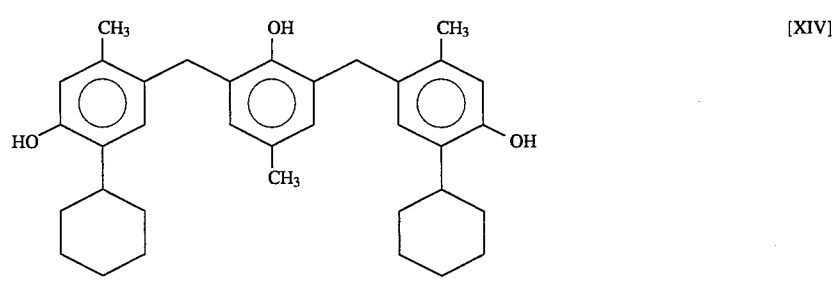

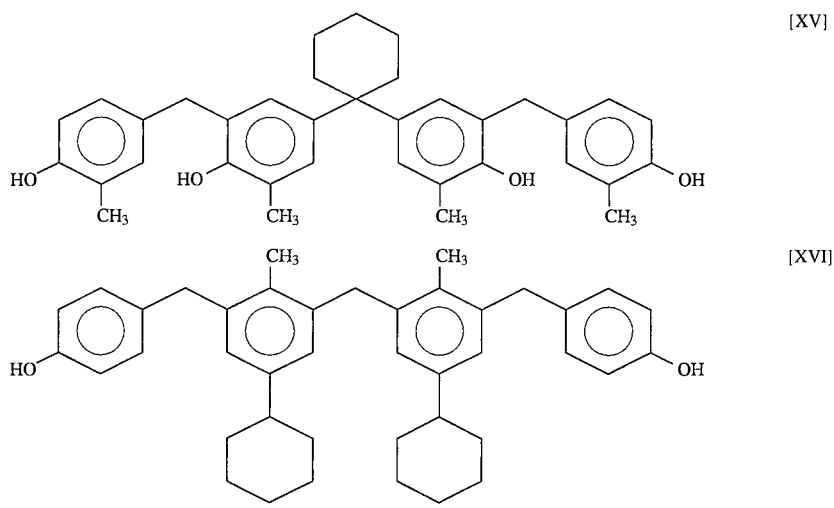
Use of compounds [X] to [XVI] gives diesters in high yield.
Examples of the selectively esterifiable compound further include the following compounds.
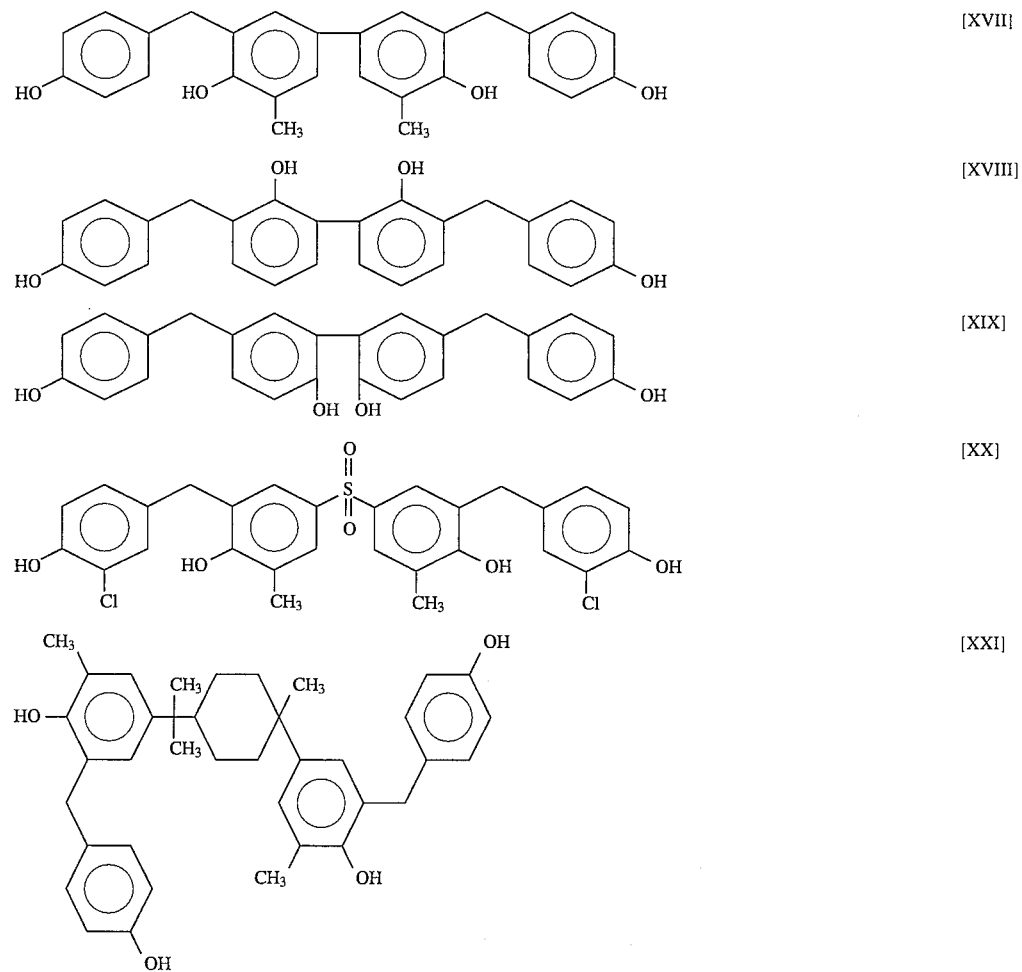

-continued

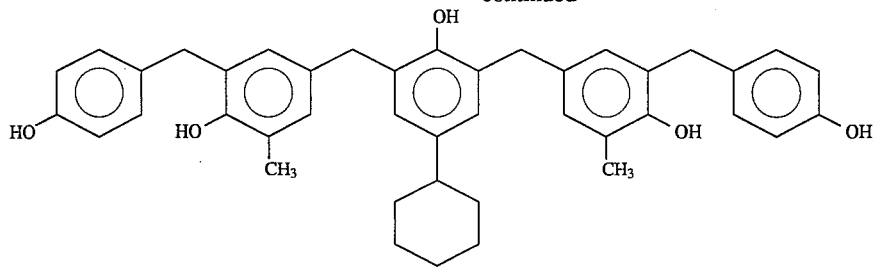
[XXII]

Use of compounds [XVII], [XX], [XXI], and [XXII] gives diesters in high yield, while use of compounds [XVIII] and [XIX] gives triesters in high yield.

On the other hand, 1,2-naphthoquinonediazide-5(and/or -4-)sulfonic ester compounds widely used as a photosensitive material for positive working photoresists are being synthesized by the esterification reaction of a polyhydroxy compound with 1,2-naphthoquinonediazide-5-(and/or -4-)sulfonyl chloride in the presence of a base catalyst (e.g., an inorganic base such as sodium hydroxide, sodium carbonate, or sodium hydrogencarbonate or an organic base such as triethylamine or dimethylaminopyridine).

In general, the esterification reaction of a polyhydroxy compound with 1,2-naphthoquinonediazide-5-(and/or -4-)sulfonyl chloride yields a photosensitive material in the form of a mixture of various esters which differ in the number and positions of ester bonds. However, it was found that when a base catalyst such as those enumerated above, e.g., triethylamine, is used to conduct the esterification of polyhydroxy compounds [III] to [XXII], esters of photosensitive materials containing specific unreacted hydroxyl group(s) can be synthesized in a certain selective manner.

Furthermore, as a result of intensive studies made by the present inventors, it has also been found that an esterification reaction having a higher selectivity for the desired ester of the photosensitive material having hydroxyl group(s) in the molecule enables to attain a more satisfactory resist performances. More particularly, it has been found that when positive working photoresists containing the photosensitive materials obtained by the esterification reactions described above are evaluated for performances, the resists containing the photosensitive materials obtained by the esterifications having a higher selectivity for the desired ester are excellent in the film thickness dependence of resolving power, development residue, etc.

SUMMARY OF THE INVENTION

Accordingly, an object of the present invention is to provide a process for quinonediazide ester synthesis by which a desired ester of a photosensitive material containing specific unreacted hydroxyl group(s) in the molecule can be synthesized highly selectively through the esterification reaction of a polyhydroxy compound with 1,2-naphthoquinone-diazide- 5-(and/or -4-)sulfonyl chloride in the presence of a base catalyst. Another object of the present invention is to provide a positive working photoresist for ultrafine processing use which is excellent in the film thickness dependence of resolving power or in development residue and has a satisfactory stability for a prolonged period of time.

As a result of intensive studies made by the present inventors in order to attain the objects described above, it has been found that the desired ester can be synthesized highly selectively by using a specific base catalyst in the esterification reaction of a polyhydroxy compound with 1,2-naphthoquinonediazide-5-(and/or -4-)sulfonyl chloride thereby solving the problems described hereinabove. The present invention has been completed based on this finding.

Namely, one object of the present invention is accomplished with a process for synthesizing a quinonediazide ester through the esterification reaction of a polyhydroxy compound with 1,2-naphthoquinonediazide-5-(and/or -4 -)sulfonyl chloride, wherein the esterification reaction is carried out in the presence of a base catalyst comprising a basic compound represented by the following formula (I) or (II):

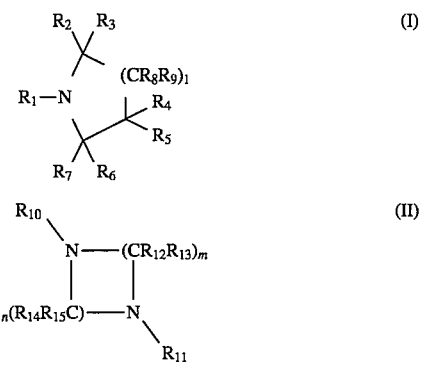

wherein $R_1$ to $R_{15}$ each represents a hydrogen atom or an alkyl group having from 1 to 4 carbon atoms (provided that $R_1$, $R_{10}$, and $R_{11}$ each is not a hydrogen atom) and l, m, and n each represents 1 or 2.

Another object of the present invention is accomplished with a positive working photoresist which comprises an alkali-soluble resin and the quinonediazide ester obtained by the process described above.

DETAILED DESCRIPTION OF THE INVENTION

The alkyl groups having from 1 to 4 carbon atoms represented by $R_1$ to $R_{15}$ in formulae (I) and (II) given above are preferably methyl, ethyl, propyl, isopropyl, n-butyl, or tert-butyl, more preferably methyl, ethyl, propyl, or isopropyl group, and furthermore preferably methyl or ethyl group. The most preferred alkyl group represented by $R_1$ to $R_{15}$ is methyl group.

In formulae (I) and (II) given above, $R_1$, $R_{10}$, and $R_{11}$ each is preferably methyl, ethyl, propyl, or isopropyl, while $R_2$ to $R_9$ and $R_{12}$ to $R_{15}$ each is preferably a hydrogen atom or methyl group.

Examples of the compounds represented by formulae (I) and (II) include the following compounds [I-1] to [I-5] and [II-1] to [II-3], but the compounds usable in this invention should not be construed as being limited thereto. These basic compounds may be used either alone or as a mixture of two or more thereof.

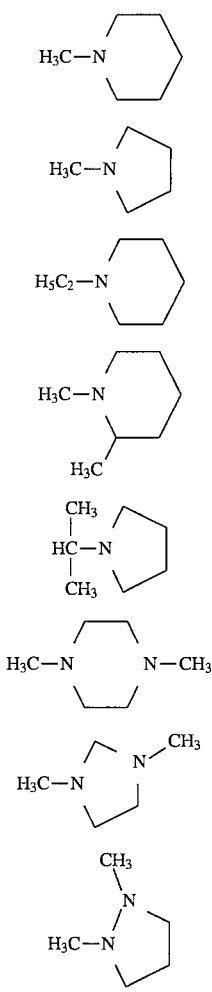

Among these specific examples, compounds [I-1], [I-2], and [II-1] are preferred.

In the process of the present invention, a 1,2-naphthoquinonediazide-5-sulfonic ester and/or a 1,2-naphthoquinonediazide-4-sulfonic ester is obtained by esterifying a polyhydroxy compound with 1,2-naphthoquinonediazide-5-(and/or -4-)sulfonyl chloride in the presence of the base catalyst described above.

The polyhydroxy compound to be used in the process of the present invention is a compound having two kinds of aromatic rings, wherein one of the aromatic rings has at least one esterifiable aromatic hydroxyl group and at least one substituent capable of inhibiting esterification of the esterifiable aromatic hydroxyl group by steric or electronic effect and the other aromatic ring has at least one esterifiable aromatic hydroxyl group and at least one substituent not capable of inhibiting, insufficient to inhibit, or capable of promoting esterification of the esterifiable aromatic hydroxyl group.

Examples of the substituent capable of inhibiting esterification of the esterifiable aromatic hydroxyl group by steric effect include 2,6-dialkyl group, o-isopropyl group and o-tert-butyl group. An example of the substituent capable of inhibiting esterification of the esterifiable aromatic hydroxyl group by electronic effect includes o-acetyl group.

Examples of the substituent not capable of inhibiting, or insufficient to inhibit esterification of the esterifiable aromatic hydroxyl group include a hydrogen atom, o-methyl group and m-alkyl group. Example of the substituent capable of promoting esterification of the esterifiable aromatic hydroxyl group include electron attractive groups, which promotes the esterification reaction by electronic effect.

Specific and preferred examples of the polyhydroxy compound include those represented by the above formulae [III] to [XXII], but the present invention is not restricted thereto.

The process of the present invention may be carried out in accordance with conventional esterification reaction as disclosed, for example, in JP-A-2-285351, except that one or more of the basic compounds represented by formula (I) and (II) described above is used as the base catalyst.

For example, predetermined amounts of a polyhydroxy compound and 1,2-naphthoquinonediazide-5-(and/or -4-)sulfonyl chloride are introduced into a flask along with a solvent, e.g., acetone, methyl ethyl ketone, methyl isobutyl ketone, 1,4-dioxane, tetrahydrofuran, dimethoxyethane, diglyme, ethyl acetate, acetonitrile, chloroform, dichloromethane, dichloroethane, chlorobenzene, N-methylpyrrolidone, or γ-butyrolactone. The base catalyst described above is added thereto dropwise or in another manner to condense the reactants. The reaction product obtained is crystallized from water, washed with water, and then further purified and dried. The reaction temperature in the above process is usually from −20° to 60° C., preferably from 0° to 40° C.

The base catalyst described above may be used in an amount of from 1.01 to 1.1 equivalent, preferably from 1.03 to 1.07 equivalent, of the 1,2-naphthoquinonediazide-5-(and/or -4-)sulfonyl chloride.

In the ordinary esterification in which an organic amine, e.g., triethylamine, is used as a base catalyst as described above, satisfactory ester selectivity has not been obtained even when the proportion of the polyhydroxy compound and 1,2-naphthoquinonediazide-5-(and/or -4-)sulfonyl chloride introduced into the reactor is changed. For accomplishing the object of the invention which is to provide a positive working photoresist excellent in the film thickness dependence and the development residue, esterification selectivity for a specific ester should be heightened. This was achieved only when the specific organic amine described above was used as a base catalyst as in the present invention.

Ester selectivity as used herein means esterification selectivity for a desired specific ester. The desired ester according to the present invention is a 1,2-naphthoquinonediazide-5-(and/or -4-)sulfonyl ester with the polyhydroxy compound wherein the aromatic hydroxyl group(s) on the aromatic ring having the substituent capable of inhibiting esterification of the aromatic hydroxyl group by steric or electronic effect in the polyhydroxy compound remain without being esterified, whereas the aromatic hydroxyl group(s) on the aromatic ring having the substituent not capable of inhibiting, insufficient to inhibit, or capable of promoting esterification of the aromatic hydroxyl group is/are esterified.

The term "film thickness dependence" as used herein means the fluctuation of the resolving power of a resist obtained through exposure, baking if desired, and development when the thickness of an unexposed resist film varies in the range of λ/4 n. The term development residue means an insoluble matter derived from the resist and remaining in developed fine patterns; this insoluble matter can be observed with a scanning electron microscope and the like.

The photosensitive materials according to the present invention obtained above is used by blending with an alkali-soluble resin to form a resin composition. The photosensitive material may be used either alone or as a mixture of two or more of them. The blending amount of the photosensitive material is from 5 to 100 parts by weight, preferably from 20 to 60 parts by weight, per 100 parts by weight of the alkali-soluble resin. If the proportion of the photosensitive material is smaller than 5 parts by weight, the resist film remaining ratio after development is considerably reduced. If the proportion thereof exceeds 100 parts by weight, the sensitivity and solubility in solvents are reduced.

If desired or necessary, the photosensitive material obtained by the synthesis process of the present invention may be used in combination with another 1,2-naphthoquinonediazide- 5-(and/or -4-)sulfonic ester. Namely, the ester of any of the polyhydroxy compounds described below with 1,2 -naphthoquinonediazide-5-(and/or-4-)sulfonyl chloride may be used together with the photosensitive material according to the present invention.

In this case, the proportion of the polyhydroxy compound/naphthoquinonediazide ester photosensitive material to the photosensitive material of the present invention is preferably from 20/80 to 80/20 (by weight). If the proportion of the photosensitive material of the present invention is less than 20% by weight based on the total amount of all photosensitive materials, the effects of the present invention cannot be fully exhibited.

Examples of the above-mentioned polyhydroxy compound include polyhydroxybenzophenones such as 2,3,4 -trihydroxybenzophenone, 2,4,4'-trihydroxybenzophenone, 2,4,6 -trihydroxybenzophenone, 2,3,4-trihydroxy-2'-methylbenzophenone, 2,3,4,4'-tetrahydroxybenzophenone, 2,2',4, 4'-tetrahydroxybenzophenone, 2,4,6,3',4'-pentahydroxybenzophenone, 2,3,4,2',4'-pentahydroxybenzophenone, 2,3,4,2', 5'-pentahydroxybenzophenone, 2,4,6,3',4',5'-hexahydroxybenzophenone, and 2,3,4,3',4',5'-hexahydroxybenzophenone;

- polyhydroxyphenyl alkyl ketones such as 2,3,4 -trihydroxyacetophenone, 2,3,4-trihydroxyphenyl pentyl ketone, and 2,3,4-trihydroxyphenyl hexyl ketone;
- bis((poly)hydroxyphenyl)alkanes such as bis(2,4 -dihydroxyphenyl)methane, bis(2,3,4-trihydroxyphenyl)methane, bis(2,4-dihydroxyphenyl)propane-1, bis(2, 3,4 -trihydroxyphenyl)propane-1, and nordihydroguaiaretic acid;
- polyhydroxybenzoic esters such as propyl 3,4,5 -trihydroxybenzoate, phenyl 2,3,4-trihydroxybenzoate, and phenyl 3,4,5-trihydroxybenzoate;
- bis(polyhydroxybenzoyl)alkanes or bis(polyhydroxybenzoyl)arenes, such as bis(2,3,4-trihydroxybenzoyl)methane, bis(3-acetyl-4,5,6-trihydroxyphenyl)methane, bis(2,3,4 -trihydroxybenzoyl)benzene, and bis(2,4,6 -trihydroxybenzoyl)benzene;
- alkylene glycol di(polyhydroxybenzoate)s such as ethylene glycol di(3,5-dihydroxybenzoate) and ethylene glycol di(3,4,5-trihydroxybenzoate);
- polyhydroxybiphenyls such as 2,3,4-biphenyltriol, 3,4,5-biphenyltriol, 3,5,3',5'-biphenyltetrol, 2,4,2',4'-biphenyltetrol, 2,4,6,3',5'-biphenylpentol, 2,4,6,2',4',6'-biphenylhexol, and 2,3,4,2',3',4'-biphenylhexol;
- bis(polyhydroxy) sulfides such as 4,4'-thiobis(1,3-dihydroxy)benzene;
- bis(polyhydroxyphenyl) ethers such as 2,2',4,4'-tetrahydroxydiphenyl ether;
- bis(polyhydroxyphenyl) sulfoxides such as 2,2',4,4'-tetrahydroxydiphenyl sulfoxide;
- bis(polyhydroxyphenyl) sulfones such as 2,2',4,4'-tetrahydroxydiphenyl sulfone;
- polyhydroxytriphenylmethanes such as tris(4 -hydroxyphenyl)methane, 4,4',4"-trihydroxy-3,5,3',5'-tetramethyltriphenylmethane, 4,4',3",4"-tetrahydroxy-3,5,3', 5'-tetramethyltriphenylmethane, 4,4',2",3",4"-pentahydroxy-3,5,3',5'-tetramethyltriphenylmethane, 2,3,4,2',3',4'-hexahydroxy-5,5'-diacetyltriphenylmethane, 2,3,4,2',3',4",3"',4"-octahydroxy-5,5'-diacetyltriphenylmethane, and 2,4,6,2',4',6'-hexahydroxy-5,5'-dipropionyltriphenylmethane;
- polyhydroxyspirobiindanes such as 3,3,3',3'-tetramethyl-1,1'-spirobiindane-5,6,5',6'-tetrol, 3,3,3',3'-tetramethyl-1,1'-spirobiindane-5,6,7,5',6',7'-hexol, 3,3,3',3'-tetramethyl-1,1'-spirobiindane-4,5,6,4',5',6'-hexol, and 3,3,3', 3'-tetramethyl-1,1'-spirobiindane-4,5,6,5',6',7'-hexol;
- polyhydroxyphthalides such as 3,3-bis(3,4 -dihydroxyphenyl)phthalide, 3,3-bis(2,3,4 -trihydroxyphenyl)phthalide, and 3',4',5',6'-tetrahydroxyspiro[phthalide-3,9'-xanthene];
- flavonoid pigments such as morin, quercetin, and rutin;
- the polyhydroxy compounds described in JP-A-4-253058, including α,α',α"-tris(4-hydroxyphenyl)-1,3,5-triisopropylbenzene, α,α',α"-tris(3,5-dimethyl-4-hydroxyphenyl)-1,3,5 -triisopropylbenzene, α,α',α"-tris(3,5-diethyl-4 -hydroxyphenyl)-1,3,5-triisopropylbenzene, α,α',α"-tris(3,5 -di-n-propyl-4-hydroxyphenyl)-1,3,5-triisopropylbenzene, α,α',α"-tris(3,5-diisopropyl-4-hydroxyphenyl)-1,3,5 -triisopropylbenzene, α,α',α"-tris(3,5-di-n-butyl-4 -hydroxyphenyl)-1,3,5-triisopropylbenzene, α,α',α"-tris(3 -methyl-4-hydroxyphenyl)-1,3,5-triisopropylbenzene, α,α',α"-tris(3-methoxy-4-hydroxyphenyl)-1,3,5-triisopropylbenzene, α,α',α"-tris(2,4-dihydroxyphenyl)-1,3,5-triisopropylbenzene, 1,3,5-tris(3,5-dimethyl-4-hydroxyphenyl)benzene, 1,3,5 -tris(5-methyl-2-hydroxyphenyl)benzene, 2,4,6-tris(3,5 -dimethyl-4-hydroxyphenylthiomethyl)mesitylene, 1-[α-methyl-α-(4'-hydroxyphenyl)ethyl]-4-[α,α'-bis(4"-hydroxyphenyl)ethyl]benzene, 1-[α-methyl-α-(4'-hydroxyphenyl)ethyl]-3-[α,α'-bis(4"-hydroxyphenyl)ethyl]benzene, 1-[α-methyl-α-(3',5'-dimethyl-4'-hydroxyphenyl)ethyl]-4-[α,α'-bis(3", 5"-dimethyl-4"-hydroxyphenyl)ethyl]benzene, 1-[α-methyl-α-(3'-methyl-4'-hydroxyphenyl)ethyl]-4-[α',α'-bis(3"-methyl-4"-hydroxyphenyl)ethyl]benzene, 1-[α-methyl-α-(3'-methoxy-4'-hydroxyphenyl)ethyl]-4-[α', α'-bis(3"-methoxy-4"-hydroxyphenyl)ethyl]benzene, 1-[α-methyl-α-(2',4'-dihydroxyphenyl)ethyl]-4-[α',α'-bis(4"-hydroxyphenyl)ethyl]benzene, and 1-[α-methyl-α-(2',4'-dihydroxyphenyl)ethyl]-3 -[α",α'-bis(4"-hydroxyphenyl)ethyl]benzene; and
- another polyhydroxy compounds such as p-bis(2,3,4 -trihydroxybenzoyl)benzene, p-bis(2,4,6-trihydroxybenzoyl)benzene, m-bis(2,3,4-trihydroxybenzoyl)benzene, m-bis(2,4,6 -trihydroxybenzoyl)benzene, p-bis(2,5-dihydroxy-3 -bromobenzoyl)benzene, p-bis(2,3,4-trihydroxy-5 -methylbenzoyl)benzene, p-bis(2,3,4-trihydroxy-5 -methoxybenzoyl)benzene, p-bis(2,3,4-trihydroxy-5 -nitrobenzoyl)benzene, p-bis(2,3,4-trihydroxy-5 -cyanobenzoyl)benzene, 1,3,5-tris(2,5-dihydroxybenzoyl)benzene, 1,3,5-tris(2,3,4-trihydroxybenzoyl)benzene, 1,2,3 -tris(2,3,4-trihydroxybenzoyl)benzene, 1,2,4-tris(2,3,4 -trihydroxybenzoyl)benzene, 1,2,4,5-tetrakis(2,3,4 -trihydroxybenzoyl)benzene, α,α'-bis(2,3,4-trihydroxybenzoyl)-p-xylene, α,α',α'-tris(2,3,4-trihydroxybenzoyl)mesitylene, 2,6-bis(2'-hydroxy-3',5'-dimethylbenzyl)-p-cresol, 2,6-bis(2'-hydroxy-5'-methylbenzyl)-p-cresol, 2,6-bis(2'-hydroxy-3',5'-di-t-butylbenzyl)-p-cresol, 2,6-bis(2'-hydroxy-5'-ethylbenzyl)-p-cresol, 2,6-bis(2',4'-dihydroxybenzyl)-p-cresol, 2,6-bis(2'-hydroxy-3'-t-butyl-5'-methylbenzyl)-p-cresol, 2,6-bis(2',3',4'-trihydroxy-5'-acetylbenzyl)-p-cresol, 2,6-bis(2',4',6'-trihydroxybenzyl)-p-cresol, 2,6-bis(2',3',4'-trihydroxybenzyl)-p-cresol, 2,6-bis(2',3',4'-trihydroxybenzyl)-3,5-dimethylphenol, 4,6-bis(4'-hydroxy-3',5'-dimethylbenzyl)pyrogallol, 4,6-bis(4'-hydroxy-3',5'-dimethoxybenzyl)pyrogallol, 2,6-bis(4'-hydroxy-3',5'-dimethylbenzyl)-1,3,4-trihydroxyphenol, 4,6-bis(2',4',6'-trihydroxybenzyl)-2,4-dimethylphenol, and 4,6-bis(2',3',4'-trihydroxybenzyl)-2,5-dimethylphenol.

Also a low molecular weight phenolic resins such as a novolak resin may also be used.

Examples of the alkali-soluble resin for use in the present invention include novolak resins, acetone-pyrogallol resins, and poly(hydroxystyrene) and derivatives thereof.

Of these, novolak resins are especially preferred, which are obtained by the addition condensation of a prescribed monomer as a major ingredient with an aldehyde in the presence of an acid catalyst.

Examples of the prescribed monomer include phenol, cresols such as m-cresol, p-cresol and o-cresol, xylenols such as 2,5-xylenol, 3,5-xylenol, 3,4-xylenol and 2,3-xylenol, alkylphenols such as m-ethylphenol, p-ethylphenol, o-ethylphenol and p-t-butylphenol, trialkylphenols such as 2,3,5-trimethylphenol and 2,3,4 -trimethylphenol, alkoxyphenols such as p-methoxyphenol, m-methoxyphenol, 3,5-dimethoxyphenol, 2-methoxy-4 -methylphenol, m-ethoxyphenol, p-ethoxyphenol, m-propoxyphenol, p-propoxyphenol, m-butoxyphenol and p-butoxyphenol, dialkylphenols such as 2-methyl-4 -isopropylphenol, and hydroxyl aromatic compounds such as m-chlorophenol, p-chlorophenol, o-chlorophenol, dihydroxybiphenyl, bisphenol A, phenylphenol, resorcinol, and naphthol. These compounds may be used alone or as a mixture of two or more thereof. However, the monomer to be condensed with an aldehyde is not limited thereto.

Examples of the aldehyde include formaldehyde, paraformaldehyde, acetaldehyde, propylaldehyde, benzaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and acetals of these aldehydes, e.g., chloroacetaldehyde diethyl acetal. Of these aldehydes, formaldehyde is preferably used.

These aldehydes may be used alone or in combination of two or more thereof.

Examples of the acid catalyst include hydrochloric acid, sulfuric acid, formic acid, acetic acid, and oxalic acid.

As the technique for synthesizing a novolak resin, one in which low-molecular components are removed or diminished is preferred. This technique is disclosed in, e.g., JP-A-60-45238, JP-A-60-97347, JP-A-60-140235, JP-A-60-189739, JP-A-64-14229, JP-A-1-276131, JP-A-2-60915, JP-A-2-275955, JP-A-2-282745, JP-A-4-101147, and JP-A-4-122938.

The novolak resin thus obtained preferably has a weight-average molecular weight of from 1,000 to 20,000. If the molecular weight thereof is lower than 1,000, unexposed parts undergo a considerable decrease in the film thickness after development. If the molecular weight thereof exceeds 20,000, a reduced developing rate results. A more preferred range of the weight-average molecular weight of the novolak resin is from 2,000 to 15,000. The weight-average molecular weight as used herein means the value measured by gel permeation chromatography in terms of polystyrene.

It is also preferred that the novolack resin has a degree of dispersion (ratio of the weight-average molecular weight Mw to the number-average molecular weight Mn, i.e., Mw/Mn) of from 1.5 to 7.0, more preferably from 1.5 to 4. If the degree of dispersion exceeds 7.0, it is difficult to attain an improved film thickness dependence, which is one of the effects of the present invention. On the other hand, if the degree of dispersion is lower than 1.5, it is unsuitable for practical use because the synthesis of resins of such degree of dispersion necessitates additional steps for a high degree of purification.

A polyhydroxy compound may be further incorporated into the resist composition of the present invention in order to accelerate dissolution into a developing solution. Preferred examples of the polyhydroxy compound include phenols, resorcinol, phloroglucinol, 2,3,4 -trihydroxybenzophenone, 2,3,4,4'-tetrahydroxybenzophenone, 2,3,4,3',4', 5'-hexahydroxybenzophenone, acetone-pyrogallol condensation resins, phloroglucide, 2,4,2',4'-biphenyltetrol, 4,4'-thiobis(1,3-dihydroxy)benzene, 2,2',4,4'-tetrahydroxydiphenyl ether, 2,2',4,4'-tetrahydroxydiphenyl sulfoxide, 2,2',4,4'-tetrahydroxydiphenyl sulfone, tris(4 -hydroxyphenyl)methane, 1,1-bis(4-hydroxyphenyl)cyclohexane, 4,4-(α-methylbenzylidene)bisphenol, α,α',α"-tris(4 -hydroxyphenyl)-1,3,5-triisopropylbenzene, α,α',α"-tris(4 -hydroxyphenyl)-1-ethyl-4-isopropylbenzene, 1,2,2 -tris(hydroxyphenyl)propane, 1,1,2-tris(3,5-dimethyl-4 -hydroxyphenyl)propane, 2,2,5,5-tetrakis(4-hydroxyphenyl)hexane, 1,2-tetrakis(4-hydroxyphenyl)ethane, 1,1,3 -tris(hydroxyphenyl)butane, and para[α,α,α',α'-tetrakis(4 -hydroxyphenyl)]xylene.

These polyhydroxy compounds may be incorporated in an amount of usually 100 parts by weight or less, preferably 70 parts by weight or less, more preferably 50 parts by weight or less, per 100 parts by weight of the alkali-soluble resin.

Examples of solvents that can be used for dissolving therein the photosensitive material of the present invention and the alkali-soluble resin include ethylene glycol monomethyl ether, ethylene glycol monoethyl ether, methyl cellosolve acetate, ethyl cellosolve acetate, diethylene glycol monomethyl ether, diethylene glycol monoethyl ether, propylene glycol methyl ether acetate, propylene glycol propyl ether acetate, toluene, xylene, methyl ethyl ketone, cyclohexanone, ethyl 2-hydroxypropionate, ethyl 2-hydroxy-2 -methylpropionate, ethyl ethoxyacetate, ethyl hydroxyacetate, methyl 2-hydroxy-3-methylbutanoate, methyl 3 -methoxypropionate, ethyl 3-methoxypropionate, ethyl 3-ethoxypropionate, methyl 3-ethoxypropionate, methyl pyruvate, ethyl pyruvate, ethyl acetate, and butyl acetate. These organic solvents may be used alone or in combination of two or more thereof.

These organic solvents may also be used as a mixture with a high-boiling solvent such as N-methylformamide, N,N-dimethylformamide, N-methylacetamide, N,N-dimethylacetamide, N-methylpyrrolidone, dimethyl sulfoxide, or benzyl ethyl ether.

A surfactant may be incorporated into the positive working photoresist composition of the present invention for the purpose of further improvement in applicability including the prevention of striation.

Examples of the surfactant include nonionic surfactants such as polyoxyethylene alkyl ethers (e.g., polyoxyethylene lauryl ether, polyoxyethylene stearyl ether, polyoxyethylene cetyl ether, polyoxyethylene oleyl ether), polyoxyethylene alkyl phenol ethers (e.g., polyoxyethylene octylphenol ether, polyoxyethylene nonylphenol ether), polyoxyethylene-polyoxypropylene block copolymers, sorbitan fatty acid esters (e.g., sorbitan monolaurate, sorbitan monopalmitate, sorbitan monostearate, sorbitan monooleate, sorbitan trioleate, sorbitan tristearate), and polyoxyethylene sorbitan fatty acid esters (e.g., polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate); fluorine surfactants such as F-Top EF301, EF303, and EF352 (manufactured by Shin Akita Chemical Co., Ltd., Japan), Megafac F171 and F173 (manufactured by Dainippon Ink & Chemicals, Inc., Japan), Fluorad FC430 and FC431 (manufactured by Sumitomo 3M Ltd., Japan), and Asahi Guard AG710, Surflon S-382, SC101, SC102, SC103, SC104, SC105, and SC106 (manufactured by Asahi Glass Co., Ltd., Japan); and organopolysiloxane polymer KP341 (manufactured by Shin-Etsu Chemical Co., Ltd., Japan) and acrylic and methacrylic acid (co)polymers Polyflow No. 75 and No. 95 (manufactured by Kyoeisha Chemical Co., Ltd., Japan). Of these surfactants, the fluorine surfactants and the silicone surfactant are especially preferred. The addition amount of these surfactants is usually 2 parts by weight or less, preferably 1 part by weight or less, per 100 parts by weight of the sum of the alkali-soluble resin and the quinonediazide compound in the composition of the present invention.

These surfactants may be added either alone or in combination of two or more thereof.

A light absorber, a crosslinking agent, an adhesion aid, and other additives may be incorporated into the positive working photoresist composition of the present invention if desired or necessary. The light absorber is added, if desired, for the purpose of preventing halation from a substrate or enhancing the recognizability of the composition applied to a transparent substrate. Examples of the light absorber include the commercial light absorbers disclosed in "Kogyoyo Shikiso No Gijutsu To Shijo (Technology and Market for Industrial Pigments)" (CMC Shuppan) and "Senryo Binran (Dyes Handbook)" (edited by Organic Synthesis Chemistry Society). Preferred examples thereof include C.I. Disperse Yellow 1, 3, 4, 5, 7, 8, 13, 23, 31, 49, 50, 51, 54, 56, 60, 64, 66, 68, 79, 82, 88, 90, 93, 102, 114, and 124, C.I. Disperse Orange 1, 5, 13, 25, 29, 30, 31, 44, 57, 72, and 73, C.I. Disperse Red 1, 5, 7, 13, 17, 19, 43, 50, 54, 58, 65, 72, 73, 88, 117, 137, 143, 199, and 210, C.I. Disperse Violet 43, C.I. Disperse Blue 96, C.I. Fluorescent Brightening Agent 112, 135, and 163, C.I. Solvent Yellow 14, 16, 33, and 56, C.I. Solvent Orange 2 and 45, C.I. Solvent Red 1, 3, 8, 23, 24, 25, 27, and 49, C.I. Pigment Green 10, and C.I. Pigment Brown 2. The light absorber may be added in an amount of usually 100 parts by weight or less, preferably 50 parts by weight or less, more preferably 30 parts by weight or less, per 100 parts by weight of the alkali-soluble resin.

The crosslinking agent is added in such an amount as not to adversely influence the formation of a positive image. It is added mainly for the purposes of sensitivity regulation and improvement in heat resistance, dry etching resistance and the like.

Examples of the crosslinking agent include compounds obtained by reacting formaldehyde with melamine, benzoguanamine, glycoluril and the like, alkyl-modification products thereof, epoxy compounds, aldehydes, azide compounds, organic peroxides, hexamethylenetetramine and the like. These crosslinking agents may be added in an amount less than 10 parts by weight, preferably less than 5 parts by weight, per 100 parts by weight of the photosensitive material. If the addition amount of the crosslinking agent exceeds 10 parts by weight, the photoresist composition comes to cause reduction in the sensitivity and generate a scum (resist residue).

The adhesion aid is added mainly for the purpose of improving the adherence between the resist to a substrate so as to prevent resist peeling especially during etching. Examples of the adhesion aid include chlorosilanes such as trimethylchlorosilane, dimethylvinylchlorosilane, methyldiphenylchlorosilane and chloromethyldimethylchlorosilane, alkoxysilanes such as trimethylmethoxysilane, dimethyldiethoxysilane, methyldimethoxysilane, dimethylvinylethoxysilane, diphenyldimethoxysilane and phenyltriethoxysilane, silazanes such as hexamethyldisilazane, N,N'-bis(trimethylsilyl)urea, dimethyltrimethylsilylamine and trimethylsilylimidazole, silanes such as vinyltrichlorosilane, γ-chloropropyltrimethoxysilane, γ-aminopropyltriethoxysilane and γ-glycidoxypropyltrimethoxysilane, heterocyclic compounds such as benzotriazole, benzoimidazole, indazole, imidazole, 2-mercaptobenzimidazole, 2-mercaptobenzthiazole, 2-mercaptobenzoxazole, urazol, thiouracil, mercaptoimidazole and mercaptopyrimidine, and urea or thiourea compounds such as 1,1-dimethylurea and 1,3-dimethylurea.

The adhesion aid may be added in an amount usually less than 10 parts by weight, preferably less than 5 parts by weight, per 100 parts by weight of the alkali-soluble resin.

For developing the positive working photoresist composition of the present invention, an aqueous solution of an alkali may be used as the developer. Examples of the alkali include inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcoholamines such as dimethylethanolamine and triethanolamine, quaternary ammonium salts such as tetramethylammonium hydroxide, tetraethylammonium hydroxide and choline, and cyclic amines such as pyrrole and piperidine. An alcohol, e.g., isopropyl alcohol, or a nonionic or another surfactant may be added to the aqueous solution of the alkali in an appropriate amount.

The positive working photoresist composition described above is applied to a substrate for use in the production of a precise integrated-circuit element (e.g., a transparent glass or ITO substrate coated with silicon/silicon dioxide) by a suitable coating means, e.g., a spinner or a coater. The coating is pre-baked, exposed to light through a predetermined mask, subjected, if necessary, to post-exposure baking (PEB), and then developed, rinsed and dried. Thus, a satisfactory resist can be obtained.

The present invention is explained below in further detail by reference to the following examples, but the present invention should not be construed as being limited thereto. Hereinafter, all "percents" are given on a weight basis unless otherwise indicated.

SYNTHESIS EXAMPLE 1

(Synthesis of Photosensitive Material a)

Into a three-necked flask were introduced 34.8 g of compound [XXIII] shown below, 53.7 g of 1,2-naphthoquinonediazide- 5-sulfonyl chloride, and 1,000 ml of acetone. The contents were stirred to give a homogeneous solution. Subsequently, 20.8 g of N-methylpiperidine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 73.2 g of a 1,2-naphthoquinonediazidesulfonic ester of compound [XXIII] (Photosensitive Material a). The intended ester in the photosensitive material is a diester.

Photosensitive Material a was analyzed by high-performance liquid chromatography using a detector employing 254-nm ultraviolet ray. As a result, the diester compound in Photosensitive Material a accounted for 73% of the whole pattern area.

For the high-performance liquid chromatography, a chromatograph device LC-6A, manufactured by Shimadzu Corp., Japan, was used along with a column Nova-Pak $C_{18}$ (4 μm) having dimensions of 8 mmφ by 100 mm, manufactured by Waters Inc. A solution consisting of 68.6% water, 30.0% acetonitrile, 0.7% triethylamine, and 0.7% phosphoric acid was passed as a carrier solvent through the column at a flow rate of 2.0 ml/min.

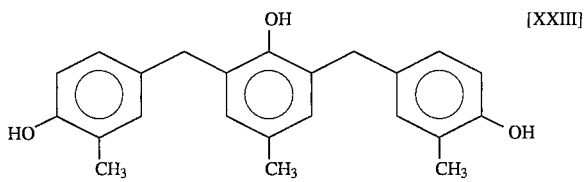

[XXIII]

SYNTHESIS EXAMPLE 2

(Synthesis of Photosensitive Material b)

Into a three-necked flask were introduced 34.8 g of compound [XXIII] shown above, 53.7 g of 1,2-naphthoquinonediazide- 5-sulfonyl chloride, and 1,000 me of acetone. The contents were stirred to give a homogeneous solution. Subsequently, 17.7 g of N-methylpyrrolidine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 73.2 g of a 1,2-naphthoquinonediazidesulfonic ester of compound [XXIII] (Photosensitive Material b).

Photosensitive Material b was analyzed by high-performance liquid chromatography using a detector employing 254-nm ultraviolet ray. As a result, the diester compound in Photosensitive Material b accounted for 65% of the whole pattern area.

SYNTHESIS EXAMPLE 3

(Synthesis of Photosensitive Material c)

Into a three-necked flask were introduced 34.8 g of compound [XXIII] shown above, 53.7 g of 1,2-naphthoquinonediazide- 5-sulfonyl chloride, and 1,000 ml of acetone. The contents were stirred to give a homogeneous solution. Subsequently, 24.0 g of 1,4-dimethylpiperazine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 73.2 g of a 1,2-naphthoquinonediazidesulfonic ester of compound [XXIII] (Photosensitive Material c).

Photosensitive Material c was analyzed by high-performance liquid chromatography using a detector employing 254-nm ultraviolet. As a result, the diester compound in Photosensitive Material c accounted for 68% of the whole pattern area.

COMPARATIVE SYNTHESIS EXAMPLE 1

(Synthesis of Photosensitive Material d)

Into a three-necked flask were introduced 34.8 g of compound [XXIII] shown above, 53.7 g of 1,2-naphthoquinonediazide- 5-sulfonyl chloride, and 1,000 ml of acetone. The contents were stirred to give a homogeneous solution. Subsequently, 21.2 g of triethylamine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 73.2 g of a 1,2-naphthoquinonediazidesulfonic ester of compound [XXIII] (Photosensitive Material d).

Photosensitive Material d was analyzed by high-performance liquid chromatography using a detector employing 254-nm ultraviolet ray. As a result, the diester compound in Photosensitive Material d accounted for 56% of the whole pattern area.

COMPARATIVE SYNTHESIS EXAMPLE 2

(Synthesis of Photosensitive Material d')

Into a three-necked flask were introduced 34.8 g of compound [XXIII] shown above, 48.4 g of 1,2-naphthoquinonediazide- 5-sulfonyl chloride, and 1,000 ml of acetone. The contents were stirred to give a homogeneous solution. Subsequently, 19.1 g of triethylamine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 69.0 g of a 1,2-naphthoquinonediazidesulfonic ester of compound [XXIII] (Photosensitive Material d').

Photosensitive Material d' was analyzed by high-performance liquid chromatography using a detector employing 254-nm ultraviolet ray. As a result, the diester compound in Photosensitive Material d' accounted for 53% of the whole pattern area.

COMPARATIVE SYNTHESIS EXAMPLE 3

(Synthesis of Photosensitive Material d")

Into a three-necked flask were introduced 34.8 g of compound [XXIII] shown above, 59.1 g of 1,2-naphthoquinonediazide- 5-sulfonyl chloride, and 1,000 ml of acetone. The contents were stirred to give a homogeneous solution. Subsequently, 23.4 g of triethylamine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 77.3 g of a 1,2-naphthoquinonediazidesulfonic ester of compound [XXIII] (Photosensitive Material d").

Photosensitive Material d" was analyzed by high-performance liquid chromatography using a detector employing 254-nm ultraviolet ray. As a result, the diester compound in Photosensitive Material d" accounted for 52% of the whole pattern area.

COMPARATIVE SYNTHESIS EXAMPLE 4

(Synthesis of Photosensitive Material e)

Into a three-necked flask were introduced 34.8 g of compound [XXIII] shown above, 53.7 g of 1,2-naphthoquinonediazide- 5-sulfonyl chloride, and 1,000 ml of acetone. The contents were stirred to give a homogeneous solution. Subsequently, 25.7 g of 4-dimethylaminopyridine dissolved in acetone was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 72.1 g of a 1,2-naphthoquinonediazidesulfonic ester of compound [XXIII] (Photosensitive Material e).

Photosensitive Material e was analyzed by high-performance liquid chromatography using a detector employing 254-nm ultraviolet ray. As a result, the diester compound in Photosensitive Material e accounted for 14% of the whole pattern area.

SYNTHESIS EXAMPLE 4

(Synthesis of Photosensitive Material f)

Into a three-necked flask were introduced 38.5 g of compound [XIII] shown below, 53.7 g of 1,2-naphthoquinonediazide- 5-sulfonyl chloride, and 1,000 ml of acetone. The contents were stirred to give a homogeneous solution. Subsequently, 20.8 g of N-methylpiperidine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 76.8 g of a 1,2-naphthoquinonediazidesulfonic ester of compound [XIII] (Photosensitive Material f). The intended ester in the photosensitive material is a diester.

Photosensitive Material f was analyzed by high-performance liquid chromatography using a detector employing 254-nm ultraviolet ray. As a result, the diester compound in Photosensitive Material f accounted for 82% of the whole pattern area.

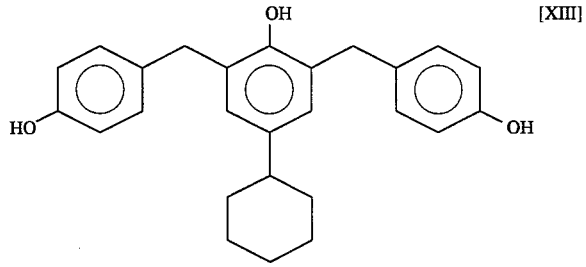

[XIII]

COMPARATIVE SYNTHESIS EXAMPLE 5

(Synthesis of Photosensitive Material g)

Into a three-necked flask were introduced 38.5 g of compound [XIII] shown above, 53.7 g of 1,2-naphthoquinonediazide- 5-sulfonyl chloride, and 1,000 ml of acetone. The contents were stirred to give a homogeneous solution. Subsequently, 21.2 g of triethylamine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 76.8 g of a 1,2-naphthoquinonediazidesulfonic ester of compound [XIII] (Photosensitive Material g).

Photosensitive Material g was analyzed by high-performance liquid chromatography using a detector employing 254-nm ultraviolet ray. As a result, the diester compound in Photosensitive Material g accounted for 68% of the whole pattern area.

SYNTHESIS EXAMPLE 5

(Synthesis of Photosensitive Material h)

Into a three-necked flask were introduced 53.7 g of compound [XV] shown below, 53.7 g of 1,2-naphthoquinonediazide- 5-sulfonyl chloride, and 1,000 ml of acetone. The contents were stirred to give a homogeneous solution. Subsequently, 20.8 g of N-methylpiperidine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 90.2 g of a 1,2-naphthoquinonediazidesulfonic ester of compound [XV] (Photosensitive Material h). The intended ester in the photosensitive material is a diester.

Photosensitive Material h was analyzed by high-performance liquid chromatography using a detector employing 254-nm ultraviolet ray. As a result, the diester compound in Photosensitive Material h accounted for 66% of the whole pattern area.

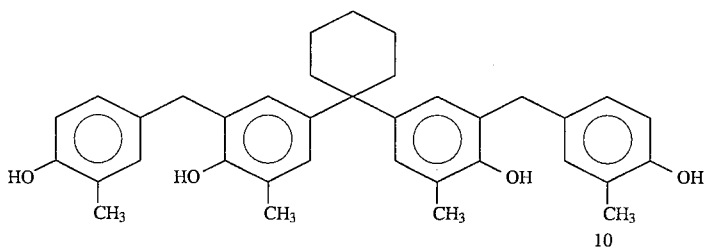

[XV]

COMPARATIVE SYNTHESIS EXAMPLE 6

(Synthesis of Photosensitive Material i)

Into a three-necked flask were introduced 53.7 g of compound [XV] shown above, 53.7 g of 1,2-naphthoquinonediazide- 5-sulfonyl chloride, and 1,000 mL of acetone. The contents were stirred to give a homogeneous solution. Subsequently, 21.2 g of triethylamine was gradually added dropwise to react the reactants at 25° C. for 3 hours. The reaction mixture was poured into 3 l of a 1% aqueous hydrochloric acid solution. The resulting precipitate was taken out by filtration, washed with water, and dried (40° C.) to obtain 90.2 g of a 1,2-naphthoquinonediazidesulfonic ester of compound [XV] (Photosensitive Material i).

Photosensitive Material i was analyzed by high-performance liquid chromatography using a detector employing 254-nm ultraviolet ray. As a result, the diester compound in Photosensitive Material i accounted for 54% of the whole pattern area.

REFERENCE SYNTHESIS EXAMPLE 1

(Synthesis of Novolak Resin A)

Into a three-necked flask were introduced 45 g of m-cresol, 55 g of p-cresol, 49 g of a 37% aqueous formaldehyde solution, and 0.13 g of oxalic acid. The contents were heated to 100° C. with stirring and reacted for 15 hours.

The reaction mixture was then heated to 200° C., and the pressure of the inside of the flask was gradually reduced to 5 mmHg to remove the water, unreacted monomers, formaldehyde, oxalic acid and the like. The resulting melt of an alkali-soluble novolak resin was cooled to room temperature to recover the resin. The thus-obtained Novolak Resin A had a weight-average molecular weight of 8,100 (calculated in terms of polystyrene as the standard) and a degree of dispersion of 6.30.

REFERENCE SYNTHESIS EXAMPLE 2

(Synthesis of Novolak Resin B)

Into a three-necked flask were introduced 50 g of m-cresol, 25 g of p-cresol, 28 g of 2,5-xylenol, 53 g of a 37% aqueous formaldehyde solution, and 0.15 g of oxalic acid. The contents were heated to 100° C. with stirring and reacted for 14 hours.

The reaction mixture was then heated to 200° C., and the pressure of the inside of the flask was gradually reduced to 1 mmHg to distill off the water, unreacted monomers, formaldehyde, oxalic acid and the like. The resulting melt of a novolak resin was cooled to room temperature to recover the resin. The novolak resin obtained had a weight-average molecular weight of 4,800 (calculated in terms of polystyrene as the standard). Subsequently, 20 g of this novolak resin was completely dissolved into 60 g of methanol. Thereto was then gradually added 30 g of water with stirring to precipitate the resin component. The upper layer was removed by decantation, and the precipitated resin component was recovered and dried at 40° C. for 24 hours under reduced pressure to obtain alkali-soluble Novolak Resin B. The thus-obtained novolak resin had a weight-average molecular weight of 9,960 (calculated in terms of polystyrene as the standard) and a degree of dispersion of 3.50. This resin had monomer, dimer, and trimer contents of 0%, 2.3%, and 3.5%, respectively, showing that 43% of the low-molecular components had been removed by the fractionating reprecipitation operation.

REFERENCE SYNTHESIS EXAMPLE 3

(Synthesis of Novolak Resin C)

Into a three-necked flask were introduced 60 g of m-cresol, 20 g of p-cresol, 25 g of 2,3,5-trimethylphenol, 56 g of a 37% aqueous formaldehyde solution, and 0.16 g of oxalic acid. The contents were heated to 100° C. with stirring and reacted for 16 hours.

The reaction mixture was then heated to 200° C., and the pressure of the inside of the flask was gradually reduced to 1 mmHg to distill off the water, unreacted monomers, formaldehyde, oxalic acid, and the like. The resulting melt of a novolak resin was cooled to room temperature to recover the resin. The novolak resin obtained had a weight-average molecular weight of 3,800 (calculated in terms of polystyrene as the standard). Subsequently, 20 g of this novolak resin was completely dissolved into 60 g of acetone. Thereto was then gradually added 60 g of hexane with stirring. This mixture was allowed to stand for 2 hours to precipitate the resin component. The upper layer was removed by decantation, and the precipitated resin ingredient was recovered and dried at 40° C. for 24 hours under reduced pressure to obtain alkali-soluble Novolak Resin C. The thus-obtained novolak resin had a weight-average molecular weight of 8,300 (calculated in terms of polystyrene as the standard) and a degree of dispersion of 3.20. This resin had monomer, dimer, and trimer contents of 0%, 2.1%, and 3.0%, respectively, showing that 56% of the low-molecular ingredients had been removed by the fractionating reprecipitation operation.

REFERENCE SYNTHESIS EXAMPLE 4

Synthesis of Novolak Resin D)

With 50 g of diethylene glycol monomethyl ether were mixed 30 g of p-cresol, 14 g of o-cresol, 50 g of 2,3-dimethylphenol, 20 g of 2,3,5-trimethylphenol, and 4.9 g of 2,6-dimethylphenol. This mixture was introduced into a three-necked flask equipped with a stirrer, a reflux condenser, and a thermometer. Subsequently, 85 g of a 37% aqueous formalin solution was added, and the mixture was stirred with heating on a 110° C. oil bath. At the time when the temperature of the contents had reached 90° C., 6.3 g of oxalic acid dihydrate was added. Reaction was thereafter allowed to proceed for 18 hours, while the temperature of the oil bath was kept at 130° C. The reflux condenser was then removed, and vacuum distillation was conducted at 200° C. to remove the unreacted monomers. The novolak resin thus obtained had an Mw of 3,280 and a degree of dispersion of 2.75.

Preparation and Evaluation of Positive Working Photoresist Compositions:

Photosensitive Materials a to i, obtained in Synthesis Examples 1 to 5 and Comparative Synthesis Examples 1 to 6 given above, Novolak Resins A to D, obtained in Reference Synthesis Examples 1 to 4 given above, solvents, and polyhydroxy compounds as an optional ingredient were mixed according to the formulations shown in Tables 1 and 2. Each mixture was stirred to give a homogeneous solution, which was then filtered through a Teflon microfilter having a pore diameter of 0.10 μm to prepare a photoresist composition. This photoresist composition was applied to silicon wafers with a spinner at different rotational speeds, and the coatings were dried at 90° C. for 60 seconds with a vacuum suction-type hot plate to obtain resist films having thicknesses of 0.97 μm and 1.02 μm, respectively.

These films were exposed through various mask patterns with a reduction projection irradiator (NSR-2005i9C, manufactured by Nikon Corporation). The exposed films were subjected to PEB treatment at 110° C. for 60 seconds, developed with a 2.38% aqueous solution of tetramethylammonium hydroxide for 1 minute, washed with water for 30 seconds, and then dried.

Each resist pattern thus obtained on the silicon wafer was examined with a scanning electron microscope to evaluate the resist. The results obtained are shown in Tables 3 and 4.

The sensitivity was defined as the inverse of the exposure amount for reproducing a 0.60-μm mask pattern, and is shown as a relative value based on the sensitivity of the 1.02 μm-thick resist of Comparative Example 1.

The resolving power means the critical resolving power as measured at the exposure amount for reproducing a 0.60-μm mask pattern.

The heat resistance is shown in terms of the maximum temperature at which the resist pattern formed on each wafer does not deform during the 4-minute baking on a hot plate.

The resist shape is shown in terms of the angle (θ) formed by the flat silicon wafer surface and the resist wall in a section of 0.50-μm resist pattern.

TABLE 1

(Formulations for Positive working Photoresist Compositions)

| Example No. | Novolak Resin | | Photosensitive Material | | Polyhydroxy Compound | | Solvent | |
|---|---|---|---|---|---|---|---|---|
| | Kind | Amount | Kind | Amount | Kind | Amount | Kind | Amount |
| 1 | A | 100 | a | 27 | — | — | S-1 | 350 |
| 2 | A | 100 | f | 26 | — | — | S-1 | 350 |
| 3 | A | 100 | h | 28 | — | — | S-2 | 380 |
| 4 | B | 78 | a | 32 | P-2 | 22 | S-1 | 350 |
| 5 | B | 78 | b | 32 | P-2 | 22 | S-1 | 350 |
| 6 | B | 82 | f | 28 | P-1 | 18 | S-2/S-4 | 285/95 |
| 7 | B | 80 | h | 29 | P-3 | 20 | S-2 | 380 |
| 8 | B | 73 | f/h(3/7) | 33 | P-1 | 27 | P-2 | 380 |
| 9 | C | 82 | f | 27 | P-3 | 18 | S-2/S-4 | 285/95 |
| 10 | C | 76 | c | 32 | P-3 | 24 | S-3 | 350 |
| 11 | C | 79 | h | 31 | P-1 | 21 | S-1 | 340 |
| 12 | D | 82 | f | 30 | P-2 | 18 | S-1 | 340 |
| 13 | D | 80 | h | 30 | P-2 | 20 | S-2/S-4 | 255/85 |

TABLE 2

(Formulations for Positive working Photoresist Compositions)

| Comparative Example No. | Novolak Resin | | Photosensitive Material | | Polyhydroxy Compound | | Solvent | |
|---|---|---|---|---|---|---|---|---|
| | Kind | Amount | Kind | Amount | Kind | Amount | Kind | Amount |
| 1 | A | 100 | e | 27 | — | — | S-1 | 350 |
| 2 | A | 100 | d" | 27 | — | — | S-1 | 350 |
| 3 | A | 100 | d' | 27 | — | — | S-1 | 350 |
| 4 | A | 100 | d | 27 | — | — | S-1 | 350 |
| 5 | B | 82 | g | 28 | P-1 | 18 | S-2/S-4 | 285/95 |
| 6 | B | 80 | i | 29 | P-3 | 20 | S-2 | 380 |
| 7 | C | 76 | d | 32 | P-3 | 24 | S-3 | 350 |
| 8 | C | 79 | i | 31 | P-1 | 21 | S-1 | 340 |

Notes:
P-1: α,α,α'-tris(4-hydroxyphenyl)-1-ethyl-4-isopropylbenzene
P-2: tris(4-hydroxyphenyl)methane
P-3: 1,1-bis(4-hydroxyphenyl)cyclohexane
S-1: ethyl cellosolve acetate
S-2: ethyl 2-hydroxypropionate
S-3: methyl 3-methoxypropionate
S-4: ethyl 3-ethoxypropionate The development residue was evaluated by examining each patterned silicon wafer with a scanning electron microscope. Wafers on which no residue was observed are rated as "A", while wafers on which a residue was observed are rated as "B".

The storage stability was evaluated by allowing each positive working photoresist composition solution at room temperature for 6 months and then examining the solution for the formation of a precipitate. Solutions in which no precipitate was observed are rated as "A", while solutions in which a precipitate was observed are rated as "B".

as compared to those of the resists of the present invention, and decreased considerably as the film thickness increases.

According to the present invention, a process for quinonediazide ester synthesis can be provided by which a desired photosensitive material containing specific unreacted hydroxyl group(s) in the molecule can be synthesized with a highly selectivity. Furthermore, a positive working photoresist for ultrafine processing use can also be provided which is excellent in the film thickness dependence of resolving power or in the development residue.

TABLE 3

(Results of Resist Performance Evaluation)

| Example No. | Relative Sensitivity | | Resolving Power (μm) | | Heat Resistance (°C.) | Shape (θ) | | Development Residue | Storage Stability |
|---|---|---|---|---|---|---|---|---|---|
| | Film Thickness 0.97 μm | Film Thickness 1.02 μm | Film Thickness 0.97 μm | Film Thickness 1.02 μm | | Film Thickness 0.97 μm | Film Thickness 1.02 μm | | |
| 1 | 1.1 | 1.2 | 0.32 | 0.32 | 150 | 89 | 89 | A | A |
| 2 | 1.2 | 1.3 | 0.32 | 0.32 | 150 | 88 | 89 | A | A |
| 3 | 1.2 | 1.3 | 0.32 | 0.32 | 150 | 89 | 89 | A | A |
| 4 | 1.2 | 1.3 | 0.28 | 0.30 | 160 | 88 | 88 | A | A |
| 5 | 1.1 | 1.2 | 0.30 | 0.30 | 160 | 89 | 89 | A | A |
| 6 | 1.2 | 1.3 | 0.28 | 0.28 | 160 | 89 | 89 | A | A |
| 7 | 1.2 | 1.3 | 0.30 | 0.30 | 160 | 89 | 89 | A | A |
| 8 | 1.2 | 1.3 | 0.28 | 0.28 | 160 | 89 | 89 | A | A |
| 9 | 1.2 | 1.3 | 0.30 | 0.30 | 160 | 88 | 88 | A | A |
| 10 | 1.1 | 1.2 | 0.32 | 0.30 | 160 | 89 | 89 | A | A |
| 11 | 1.2 | 1.3 | 0.30 | 0.30 | 160 | 88 | 88 | A | A |
| 12 | 1.1 | 1.2 | 0.28 | 0.28 | 160 | 89 | 89 | A | A |
| 13 | 1.2 | 1.3 | 0.28 | 0.28 | 160 | 89 | 89 | A | A |

TABLE 4

(Results of Resist Performance Evaluation)

| Comparative Example No. | Relative Sensitivity | | Resolving Power (μm) | | Heat Resistance (°C.) | Shape (θ) | | Development Residue | Storage Stability |
|---|---|---|---|---|---|---|---|---|---|
| | Film Thickness 0.97 μm | Film Thickness 1.02 μm | Film Thickness 0.97 μm | Film Thickness 1.02 μm | | Film Thickness 0.97 μm | Film Thickness 1.02 μm | | |
| 1 | 0.9 | 1.0 | 0.35 | 0.40 | 150 | 86 | 85 | B | B |
| 2 | 1.1 | 1.2 | 0.35 | 0.38 | 150 | 86 | 86 | A | B |
| 3 | 1.1 | 1.2 | 0.35 | 0.33 | 150 | 87 | 88 | A | A |
| 4 | 1.2 | 1.3 | 0.33 | 0.35 | 150 | 88 | 88 | A | A |
| 5 | 1.1 | 1.2 | 0.33 | 0.35 | 160 | 89 | 88 | A | A |
| 6 | 1.2 | 1.3 | 0.33 | 0.35 | 160 | 88 | 88 | A | A |
| 7 | 1.0 | 1.1 | 0.33 | 0.35 | 160 | 88 | 88 | A | A |
| 8 | 1.0 | 1.1 | 0.33 | 0.35 | 160 | 88 | 88 | A | A |

As shown in Table 3, the resists of Examples 1 to 13 according to the present invention showed excellent performances with respect to all of the sensitivity, the resolving power, the heat resistance, the resist shape, the development residue, and the storage stability. In particular, these resists showed a high resolving power even when the resist film thickness changed.

In contrast, Comparative Examples 1 to 8 failed to give results satisfactory in all of the evaluation items at the same time. In particular, the resolving powers of the resists of the Comparative Examples were lower at either film thickness While the invention has been described in detail and with reference to specific embodiments thereof, it will be apparent to one skilled in the art that various changes and modifications can be made therein without departing from the spirit and scope thereof.

What is claimed is:

1. A process for synthesizing a quinonediazide ester by the esterification reaction of a polyhydroxy compound with at least one of 1,2-naphthoquinonediazide-5-sulfonyl chloride or 1,2-naphthoquinonediazide-4-sulfonyl chloride, wherein said esterification reaction is carried out in the presence of a base catalyst comprising a basic compound represented by the following formula (I) or (II):

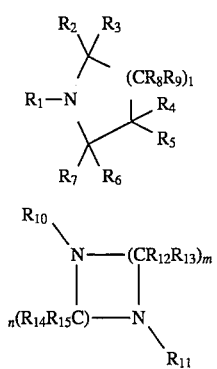
(I)
(II)
wherein $R_1$ to $R_{15}$ each represents a hydrogen atom or an alkyl group having from 1 to 4 carbon atoms provided that $R_1$, $R_{10}$, and $R_{11}$ are not a hydrogen atom and l, m, and n each represents 1 or 2.
2. The process of claim 1, wherein said basic compound is N-methylpyrrolidine, N-methylpiperidine, or 1,4-dimethylpiperazine.
* * * * *